under 35 U.S.C. 154(b) by 0 days.

(12) United States Patent
Ojima et al.

(10) Patent No.: US 7,053,371 B2
(45) Date of Patent: May 30, 2006

(54) SCANNING ELECTRON MICROSCOPE WITH MEASUREMENT FUNCTION

(75) Inventors: Yuuki Ojima, Hitachinaka (JP); Katsuhiro Sasada, Hitachinaka (JP); Kazuhiro Ueda, Hitachinaka (JP); Tsuyoshi Morimoto, Hitachinaka (JP)

(73) Assignees: Hitachi High-Technologies Corporation, Tokyo (JP); Hitachi Science Systems, Ltd., Ibaraki (JP)

(*) Notice: Subject to any disclaimer, the term of this patent is extended or adjusted under 35 U.S.C. 154(b) by 0 days.

(21) Appl. No.: 10/779,848

(22) Filed: Feb. 18, 2004

(65) Prior Publication Data
US 2004/0164245 A1 Aug. 26, 2004

(30) Foreign Application Priority Data
Feb. 21, 2003 (JP) ............................. 2003-044290

(51) Int. Cl.
G03F 7/20 (2006.01)
G03F 7/40 (2006.01)

(52) U.S. Cl. .................. 250/310; 430/30; 430/328; 430/22; 430/394; 250/311; 250/307; 250/492.3

(58) Field of Classification Search .............. 250/311, 250/307, 310; 430/619, 566, 567, 193, 236.1, 430/296, 394, 22
See application file for complete search history.

(56) References Cited

U.S. PATENT DOCUMENTS 5,006,795 A * 4/1991 Yoshizawa et al. ......... 324/751
5,659,172 A * 8/1997 Wagner et al. .............. 250/307
6,172,363 B1 * 1/2001 Shinada et al. ............. 250/310
2003/0010914 A1 * 1/2003 Takane et al. .............. 250/310
2003/0015660 A1 * 1/2003 Shishido et al. ............ 250/311
2003/0111602 A1 * 6/2003 Sato et al. .................. 250/310
2003/0141451 A1 * 7/2003 Sato et al. .................. 250/310
2003/0219658 A1 * 11/2003 Shishido et al. ............. 430/30

FOREIGN PATENT DOCUMENTS

| JP | 2-6705 | 1/1990 |
| JP | 6-347246 | 12/1994 |
| JP | 8-22794 | 1/1996 |
| JP | 10-213427 | 8/1998 |
| JP | 11-201919 | 7/1999 |
| JP | 11-237231 | 8/1999 |

* cited by examiner

*Primary Examiner*—Nikita Wells
*Assistant Examiner*—Johnnie L Smith, II
(74) *Attorney, Agent, or Firm*—Dickstein Shapiro Morin & Oshinsky LLP

(57) ABSTRACT

A scanning electron microscope which efficiently makes measurements for plural measurement items at a time and allows easy entry, confirmation and revision of auto measurement parameters. Parameters for creation of a line profile from an image captured by the scanning electron microscope are entered as auto measurement parameters (AMP) to be used as common conditions for all measurement items. Also, plural combinations of edge detection methods and measurement calculation methods are entered as auto measurement parameters to make measurements for plural items.

5 Claims, 14 Drawing Sheets

FIG. 2

| Edge Detect Method : Bottom (B 1) | | Edit |
|---|---|---|
| Method : Threshold | | Edit |

Edge Detect Parameter

|  | Left | Right |
|---|---|---|
| Threshold | 50% | 50% |
| EdgeNumber | 1 | 1 |
| BaseLineStartPoint | — | — |
| BaseLineArea | — | — |
| EdgeSearchDirection | Normal | Normal |

Mesurement Select

| Width | Mean | W1 | ■ |
|---|---|---|---|
| Width | Mean' | W2 | ☐ |
| Width | Max | W3 | ☐ |
| Width | Min | W4 | ☐ |
| WidthRoughness | 3σ | WR1 | ■ |
| WidthRoughness | 3σ' | WR2 | ☐ |
| WidthRoughness | Max-Min | WR3 | ☐ |
| EdgeRoughness Left | 3σ | El1 | ☐ |
| EdgeRoughness Left | 3σ' | El2 | ☐ |
| EdgeRoughness Left | Max-Min | El3 | ☐ |
| EdgeRoughness Right | 3σ | Er1 | ☐ |
| EdgeRoughness Right | 3σ' | Er2 | ☐ |
| EdgeRoughness Right | Max-Min | Er3 | ☐ |

OK    Cancel

FIG. 4

| Information | | | |
|---|---|---|---|
| Method : L/S (Multi) | | | |
| Object | | Mesurement | |
| Bottom<br>Top<br>Space<br>Pitch (Left)<br>Pitch (Right)<br>Slope (Left)<br>Slope(Right) | B<br>T<br>S<br>Pl<br>Pr<br>Sl<br>Sr | Width<br>  1.Mean<br>  2.Mean'<br>  3.Max<br>  4.Min<br>Width Roughness<br>  1. $3\sigma$<br>  2. $3\sigma$'<br>  3.Max-Min<br>Edge Roughness (Left)<br>  1. $3\sigma$<br>  2. $3\sigma$'<br>  3.Max-Min<br>Edge Roughness (Right)<br>  1. $3\sigma$<br>  2. $3\sigma$'<br>  3.Max-Min | W1<br>W2<br>W3<br>W4<br><br>WR1<br>WR2<br>WR3<br><br>El1<br>El2<br>El3<br><br>Er1<br>Er2<br>Er3 |
| | | | Close |

| SHEET NO. : 1 | | | | LOAD   SAVE   INFORMATION | | |
|---|---|---|---|---|---|---|
| EDGE DETECT | | MEASUREMENT | | | DATA | NO. |
| 1 | B(1) | 1 | B(1) | W1 | 120.2 | 1 |
| 2 | T(1) | 2 | B(1) | WR1 | 2.0 | 2 |
| 3 | | 3 | T(1) | W1 | | 3 |
| 4 | | 4 | T(1) | WR1 | | 4 |
| 5 | | 5 | | | | |
| 6 | | 6 | | | | |
| 7 | | 7 | | | | |
| 8 | | 8 | | | | |
| 9 | | 9 | | | | |
| 10 | | 10 | | | | |
| 11 | | 11 | | | | |
| 12 | | 12 | | | | |
| 13 | | 13 | | | | |
| 14 | | 14 | | | | |
| 15 | | 15 | | | | |

Calculation of W1 (mean)

$$\frac{(1)+(2)+(3)+(4)+(5)}{5}$$

SCANNING ELECTRON MICROSCOPE WITH MEASUREMENT FUNCTION

FIELD OF THE INVENTION

The present invention relates to a scanning electron microscope with a measurement function and a measurement method which uses it.

BACKGROUND OF THE INVENTION

The following patent documents (gazettes) describe conventional techniques in this field:
Patent Document 1: JP-A No. 347246/1994
Patent Document 2: JP-A No.22794/1996
Patent Document 3: JP-A No.237231/1999
Patent Document 4: JP-A No.213427/1998
Patent Document 5: JP-A No.201919/1999

A scanning electron microscope with a measurement function (hereinafter called a measurement SEM) has been used for control of semiconductor sample dimensions or other similar purposes. There are two dimensional measurement modes: a manual measurement mode and an auto measurement mode. In the manual measurement mode, an operator visually makes a measurement using a measurement cursor. In the auto measurement mode, a measurement SEM captures an image of a pattern to be measured (hereinafter called an "SEM image") and creates, from the image, a line profile which is considered to reflect the cross section of the pattern; the position of an edge of the pattern is detected from the line profile and according to the detected edge, the measurement (length) of the pattern is calculated. In the auto mode, line profile creation, edge detection, and measurement calculation are carried out according to predetermined auto measurement parameters (hereinafter called AMP). Refer to Patent Document 1.

Patent Document 2 describes a groove shape measuring method in which a secondary electron image of a groove is obtained from observation of its surface by a scanning electron microscope and the width of the groove or track pitch as a groove shape factor is measured. This method comprises the following four steps. In the first step, the secondary electron image of the groove is converted into image file data in a sequential file form. In the second step, according to the image file data obtained in the first step, a profile image of contrast is obtained by successively scanning the number of "bright" spots existing in a measuring unit area enclosed by a desired length in the groove direction perpendicular to the groove width direction and a length in the width direction, equivalent to one dot as the minimum pixel unit. In the third step, for the profile image of contrast obtained in the second step, an edge detecting slice level for measurement of the opening width of the groove, HLV, and an edge detecting slice level for measurement of the bottom width of the groove, LLV, are calculated from the following equations, where AVG represents the average of the number of "bright" spots existing in each of the measuring unit areas:

$$HLV = AVG \times SLU (1 < SLU < 2)$$

$$LLV = AVG \times SLB (0 < SLB < 2)$$

In the fourth step, the track pitch between neighboring grooves is calculated using one of the edges of the groove opening or bottom which is detected according to the slice levels HLV and LLV calculated in the third step.

Patent Document 3 describes a method of determining the position of a pattern edge and Patent Document 4 and Patent Document 5 each describe a method of obtaining a line profile.

In recent years, there has been an increasing tendency to use an auto dimensional measurement method and the accuracy of auto measurement has been improving year by year. In auto measurement, there are two operation modes: a semi-auto mode in which movement to a measuring point or identification of a measuring point is done by an operator, and a full-auto mode in which measurements are made fully automatically, or with no operator assistance, by executing a recipe file which stores wafer surface data, measuring point position data or other information.

The recent trend is as follows: as semiconductor samples become smaller, measurement SEMs are more functional; they measure not only the line width of a pattern or the diameter of a hole automatically but also width roughness, edge roughness and so on for evaluation of the pattern shape.

In the conventional techniques, a set of auto measurement parameters (AMP) is needed to make a measurement for an item in the auto mode. Therefore, in semi-auto measurement, if several types of measurements are to be made, it is necessary to specify a set of AMP for each measurement type, which is very troublesome. In full-auto measurement, if several types of measurements are to be made, required AMP data is stored in a recipe file and thus operation is easy, but it is troublesome to revise and check the stored AMP data. A resulting measurement value is displayed in a window of the SEM upon execution of measurement; when several types of measurements are made, it is not easy to check numerical measurement values so the operator has to wait for completion of the whole measurement process until a list of measurement results appears.

SUMMARY OF THE INVENTION

An object of the present invention is to provide a scanning electron microscope which efficiently and easily makes measurements for plural measurement items and a measurement method which use it.

Another object of the present invention is to make it easy to store, check, and revise auto measurement parameters to make measurements for plural measurement items.

According to one aspect of the present invention, parameters for creation of a line profile from an SEM image are specified for common use for plural measurement items and entered as auto measurement parameters (AMP entry). Here, "AMP entry" means that parameters are specified in an AMP window and saved in a storage. Also, plural edge detection methods and measurement calculation methods can be entered in the AMP window so that measurements for plural items can be made easily.

According to another aspect of the present invention, there is provided a scanning electron microscope with a measurement function, where plural measurement items including plural measurement calculation methods are specified for an edge detected by at least one edge detection method, or a single edge detection operation, in an auto measurement parameter (AMP) configuration window; a line profile is created from an SEM image; an edge is detected as specified from the line profile; and measurements are calculated successively from each detected edge according to the specified plural measurement calculation methods. Also, a measurement method which uses it is provided.

BRIEF DESCRIPTION OF THE DRAWINGS

The invention will be more particularly described with reference to the accompanying drawings, in which:

FIG. 2 shows a window where edge detection parameters are specified and measurement calculation methods are selected;

FIG. 4 shows a window displaying items which can be measured by a measurement method L/S (Multi);

FIG. 11 shows measurement results displayed in a window;

DETAILED DESCRIPTION OF THE PREFERRED EMBODIMENTS

Next, preferred embodiments of the present invention will be described referring to the accompanying drawings.

Figure 15:
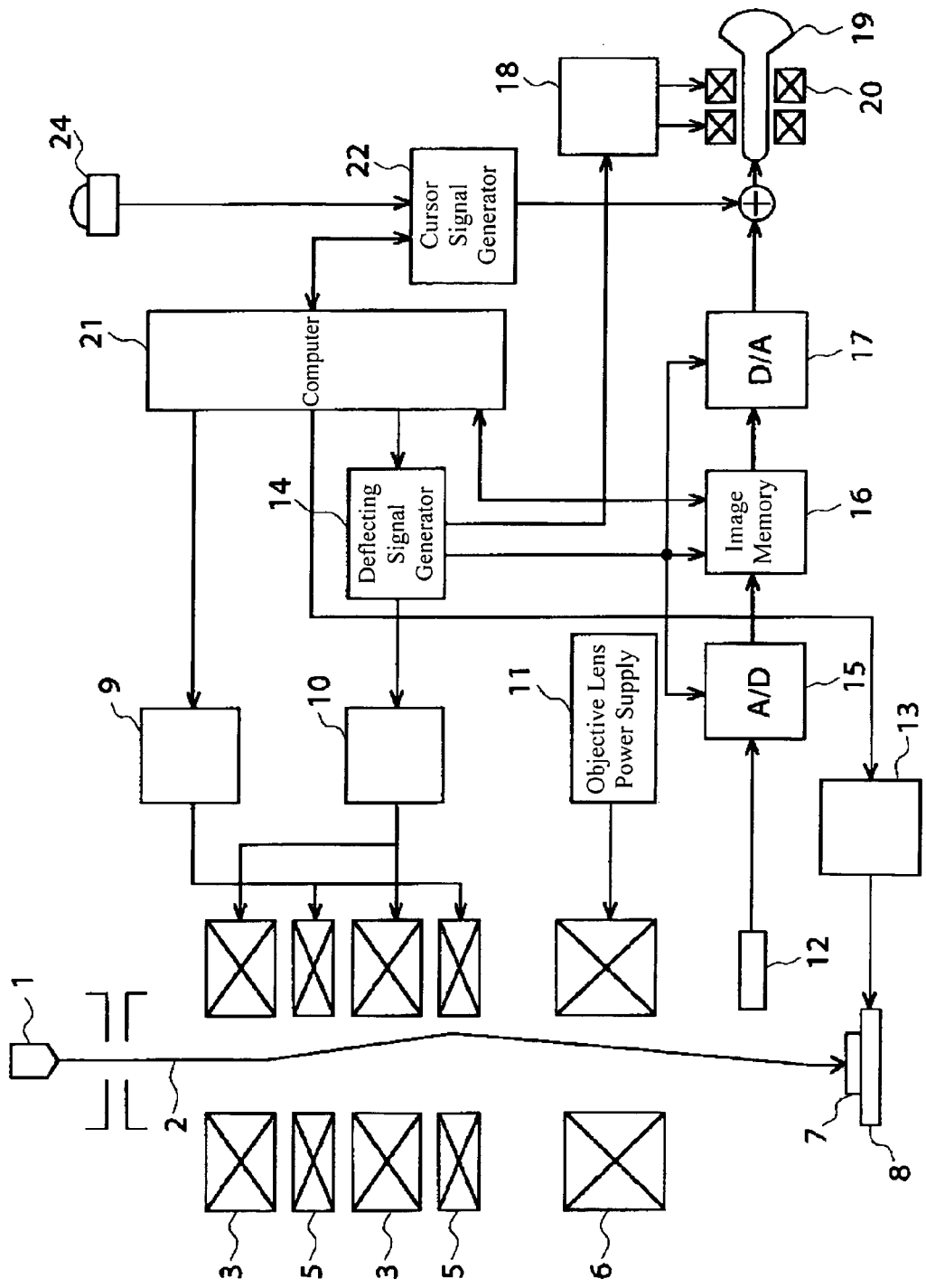
FIG. 15 is a known block diagram showing the general structure of a scanning electron microscope with a measurement function.

FIG. 15 shows the general structure of a scanning electron microscope with a measurement function according to an embodiment of the present invention (see Patent Document 1). An electron beam 2 emitted from an electron gun 1 is narrowed by an objective lens 6 and thrown on a sample 7. The objective lens 6 is excited by an objective lens power supply 11. A deflecting signal generator 14 sends a deflecting signal depending on a scanning area or scanning position of the electron beam 2 as indicated by a computer 21 through a deflecting amplifier 10 to a deflecting coil 5 to excite it so that the sample 7 is scanned with the electron beam 2 two-dimensionally.

A secondary signal (secondary electron signal, reflection electron signal, etc.), which is generated from the sample 7 in response to irradiation of the electron beam 2, is detected by a detector 12 and converted into an electric signal before being converted from an analog signal into a digital signal by an A/D converter 15 and stored in an image memory 16. The content of the image memory 16 in the digital form is always reconverted into an analog signal by a D/A converter 17 and applied to a grid as a brightness signal for an image display CRT (cathode ray tube) 19. Here, the A/D converter 15, image memory 16, and D/A converter 17 receive a timing signal from the deflecting signal generator 14 so as to A/D convert, store, and D/A convert it and display an image. A deflecting coil 20 for the image display CRT 19 is excited by a signal obtained by amplifying the deflecting signal generated from the deflecting signal generator 14 by a deflecting amplifier 18.

On the other hand, a sample stage 8 on which the sample 7 rests is moved by a stage drive circuit 13 so that the scanning position of the electron beam 2 on the sample 7 changes and the field of view moves. The field of view can also be moved by exciting an image shift coil 3 through a DC amplifier 9 and shifting the scanning position of the electron beam 2 on the sample 7. Movement of the field of view is controlled by the computer 21.

A cursor signal generated by a cursor signal generator 22 is varied by a signal from a trackball 24 or the computer 21 to change the position of the cursor on the image display CRT 19. The computer 21 acquires data on the cursor position on the image display CRT 19 depending on the status of the cursor signal generator 22. The computer 21 can read some or all image data in the image memory 16. Thus, using data on some image area around the cursor position in combination with the cursor position data, image line integration is done to generate a signal waveform, change a corresponding position in the image memory 16, and view the signal waveform (line profile) on the image display CRT 19. Another approach to viewing a signal waveform on the CRT 19 is that a special memory for viewing a signal waveform is provided to change a corresponding position in the special memory and the special memory is XORed with the image memory 16.

Figure 1:
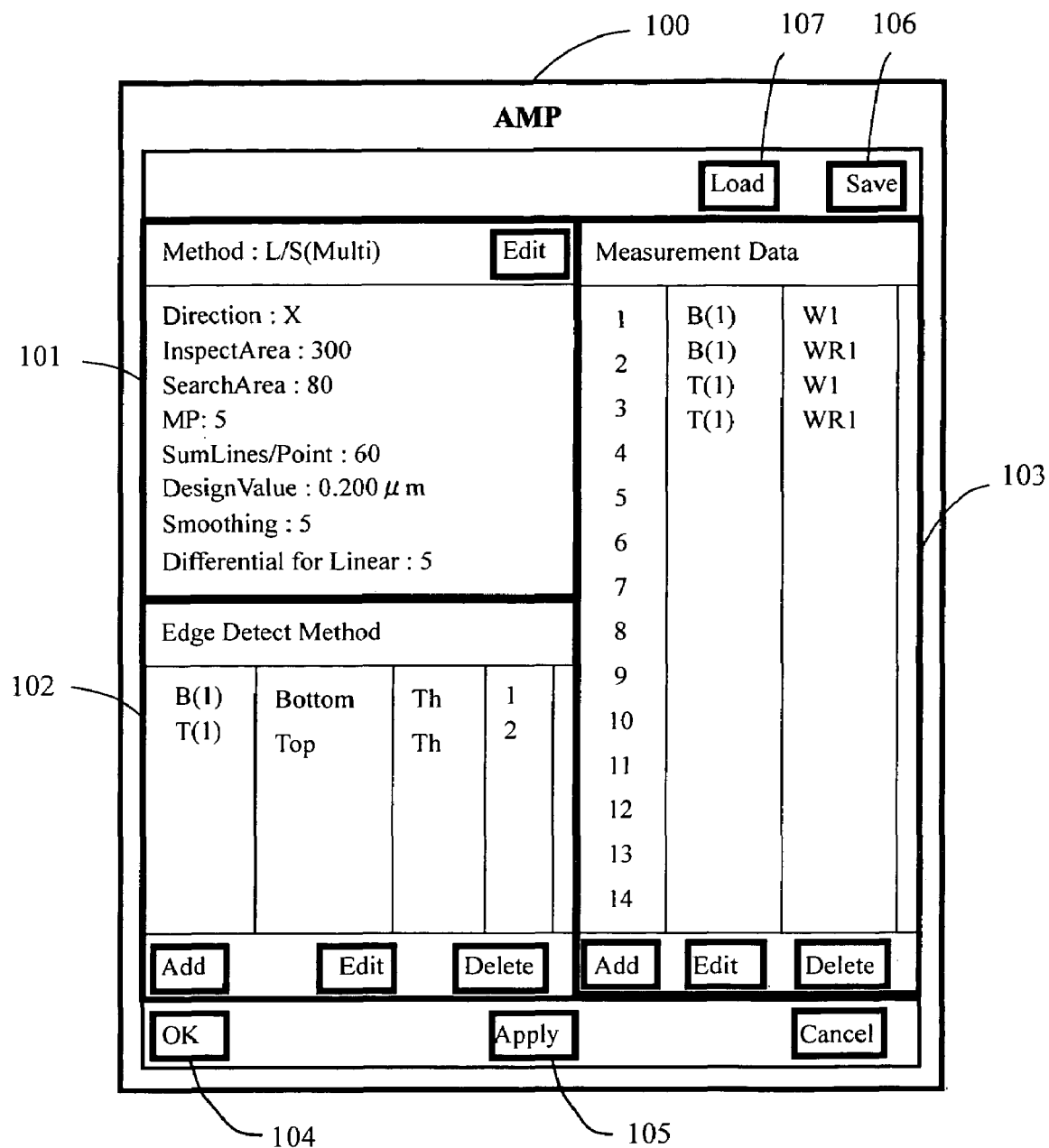
FIG. 1 shows an AMP configuration window according to an embodiment of the present invention.

FIG. 1 shows an AMP configuration window (hereinafter called the AMP window) 100. Here, the process of specifying AMP in the AMP window 100 is called "specification of AMP" or "AMP entry."

The AMP window 100 is mainly composed of three areas: a window area C, that is a first window area 103, where plural measurement items are specified; a window area A, that is a second window area 101, where auto measurement parameters are specified as common conditions for the specified plural measurement items; and a window area B, that is a third window area 102, where plural measurement items are displayed and revisions are made.

In the window area A (101), the following parameters are specified as conditions. These will be explained in detail later.

Method: L/S (Multi) (selected measurement method)

Direction: X

Inspect Area: 300

Search Area: 80

MP: 5

Sum Lines/Point: 60

Design Value: 0.200 μm

Smoothing: 5

Differential for Linear: 5

In the window area B (102), plural edge detection method options are specified.

| Edge Detect Method | | |
| --- | --- | --- |
| B(1)Bottom | Th | 1 |
| T(1)Top | Th | 2 |

In the window area C (103), plural measurement items including plural measurement calculation methods are shown.

| Measurement Data | | |
|---|---|---|
| 1 | B(1) | W1 |
| 2 | B(1) | WR1 |
| 3 | T(1) | W1 |
| 4 | T(1) | WR1 |

In the AMP configuration shown in FIG. 1, Multi Point Measurement for line and space type patterns (L/S (Multi) is selected as a measurement method and AMP entry (specification and storage of auto measurement parameters) is made for auto measurement of a (mean) width of the line pattern bottom and a width of the roughness (3σ) as well as a (mean) top width and a width of the roughness (3σ).

Figure 3:
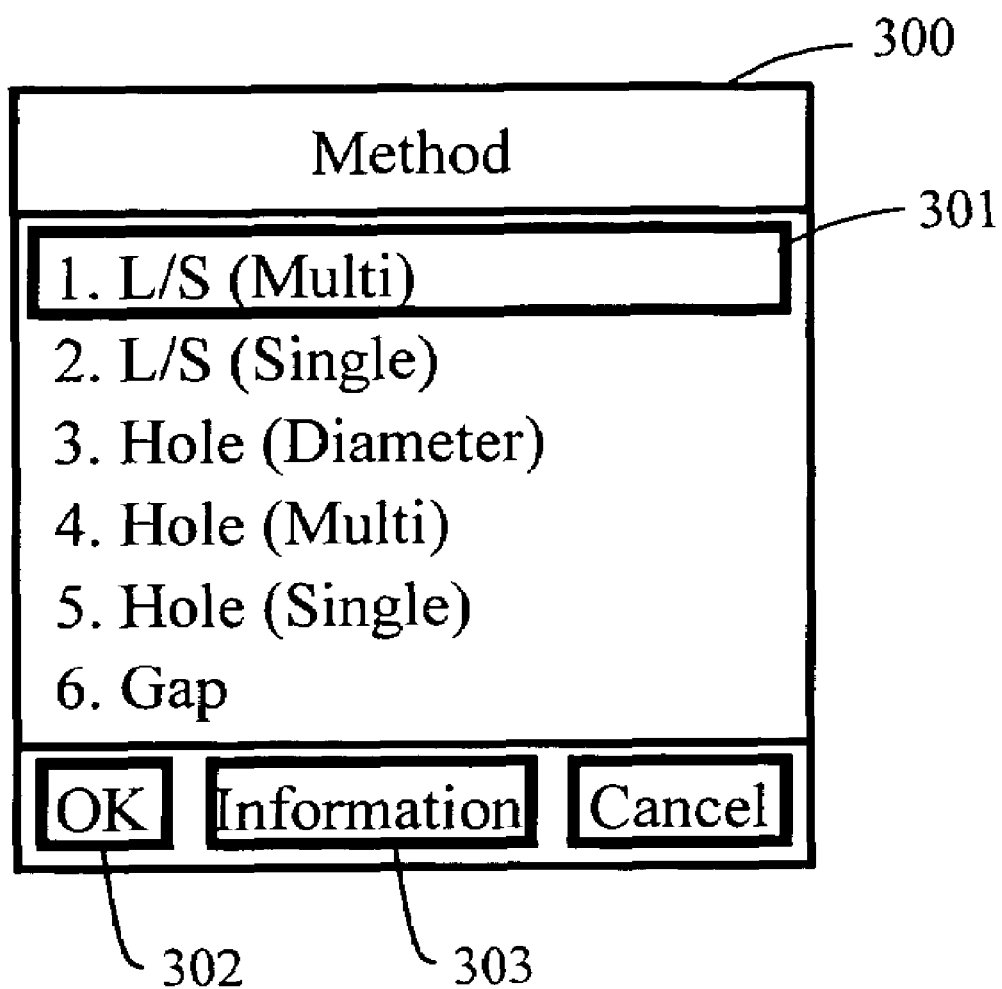
FIG. 3 shows a window for selection of a measurement method.

First of all, the operator opens an SEM image display window 600 (FIG. 6) on the CRT for AMP entry and presses an AMP button 601 in the window 600 to open the AMP window 100 on the CRT. Then, AMP entry is made as follows. First, a measurement method is selected. The selection is made as follows. The Edit button for Method in the window area A (101) of the AMP window 100 is pressed and a measurement method selection window 300 (FIG. 3) appears. From a list of measurement methods in the measurement method selection window 300, a measurement method which matches the pattern shape is selected; in this case, L/S (Multi) 301 is selected to measure (mean) top and bottom widths and a width roughness (3σ). Then, the OK button 302 is pressed. When the Information button 303 is pressed after selection of the measurement method in the window 300, measurement items for which measurement by each measurement method is possible are viewed as shown in FIG. 4.

In the Method window (FIG. 3), available measurement methods are shown as follows:

| 1. L/S (Multi) | Line |
|---|---|
| 2. L/S (Single) | Line |
| 3. Hole (Diameter) | Hole |
| 4. Hole (Multi) | Hole |
| 5. Hole (Single) | Hole |
| 6. Gap | Gap |

When L/S (Multi) is selected as the measurement method, objects to be measured (Object) are listed in the Information window (FIG. 4) as follows:

| Bottom | B |
|---|---|
| Top | T |
| Space | S |
| Pitch (Left) | Pl |
| Pitch (Right) | Pr |
| Slope (Left) | Sl |
| Slope (Right) | Sr | and also measurement items to be calculated (Measurement) are listed as follows:

| Width | |
|---|---|
| 1. Mean | W1 |
| 2. Mean' | W2 |
| 3. Max | W3 |
| 4. Min | W4 |
| Width Roughness | |
| 1. 3σ | WR1 |
| 2. 3σ' | WR2 |
| 3. Max-Min | WR3 |
| Edge Roughness (Left) | |
| 1. 3σ | El1 |
| 2. 3σ' | El2 |
| 3. Max-Min | El3 |
| Edge Roughness (Right) | |
| 1. 3σ | Er1 |
| 2. 3σ' | Er2 |
| 3. Max-Min | Er3 |

In multi point measurement, plural edge positions are detected from plural line profiles. From data on plural edge positions, measurement values are calculated by the method selected in the AMP entry process. From one edge position, plural measurement values are calculated.

An example of a procedure of calculating a measurement from data on each edge position is explained below. Since different measurement results can be shown as measurement values, they are identified by number.

The terms used here have the following meanings:

When L/S (Multi) is selected and MP=32:

W: Width
    W1: mean of widths at 32 points
    W2: mean of widths at 30 points (excluding the maximum and minimum values)
    W3: maximum width among widths at 32 points
    W4: minimum width among widths at 32 points WR: Width Roughness
    WR1: σ×3 for widths at 32 points
    WR2: σ×3 for widths at 30 points (excluding the maximum and minimum values)
    WR3: Maximum value among widths at 32 points minus the minimum value E1: Edge Roughness Left Edge (pattern left edge roughness)
    E11: σ×3 for edge positions (X coordinate values) at 32 points on the left of the pattern
    E12: σ×3 for edge positions (X coordinate values) at 30 points on the left of the pattern excluding the maximum and minimum values
    E13: Maximum edge position X coordinate value minus the minimum value Er: Edge Roughness Right Edge (pattern right edge roughness)

Alternatively, edge roughness after compensation for pattern inclination may be expressed.

Figure 7:
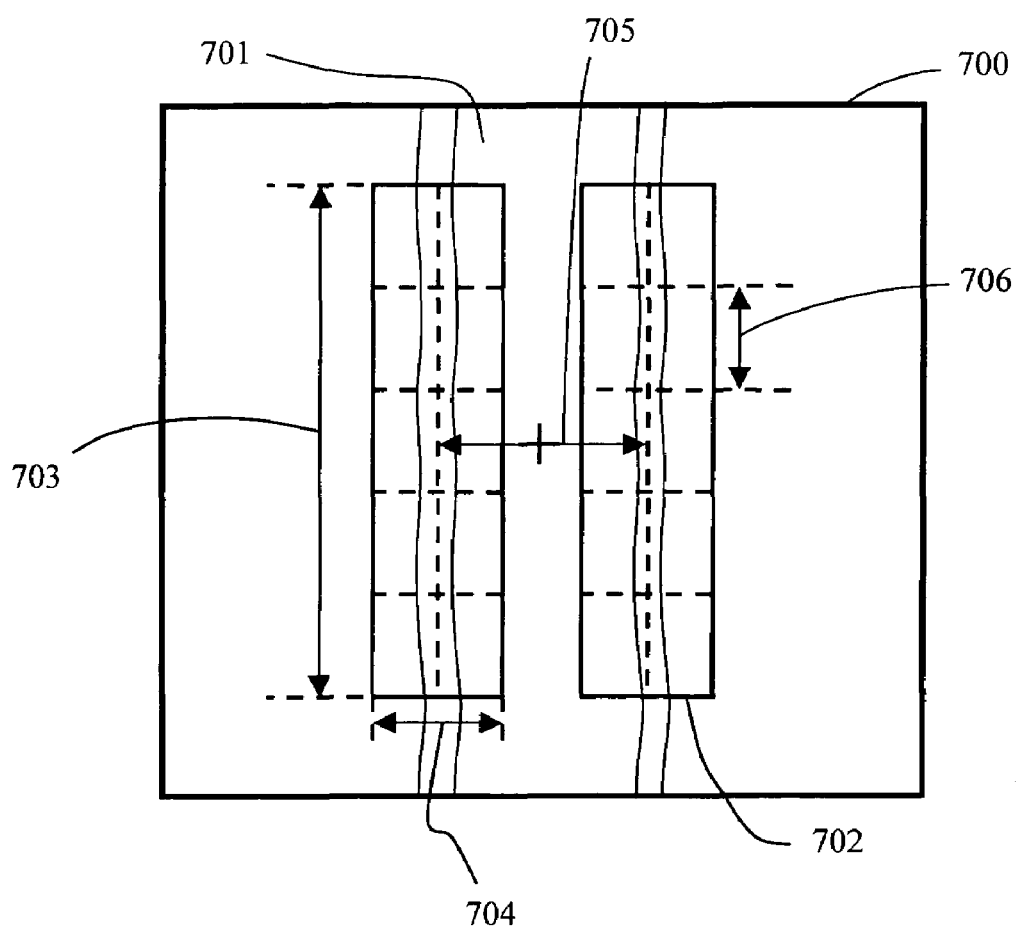
FIG. 7 illustrates measurement box cursors on an SEM image.

Next, a measuring area and conditions (parameters) for creation of a line profile are specified in the window area A (101) of the AMP window 100. The items shown in the window area A (101) are parameters concerning measuring points and a measuring area. An explanation is given below with reference to FIG. 1 and FIG. 7. "Direction" is used to specify the direction of creation of a line profile and the direction of edge detection. If a vertical line pattern 701 in an SEM image 700 (FIG. 7) is to be measured, X is chosen for Direction. Then, "Inspect Area" 703 and "Search Area" 704 are used to specify the area for line profile creation and the area for edge detection, respectively. For example, the measuring area is specified by entering 300 for Inspect Area 703 and 80 for Search Area. "Design Value" 705 represents the distance between the right and left box cursors. If a larger value (for example, 0.200 µm) is entered for Design Value 705, the distance between the left edge detection area and right edge detection area is increased.

In the area specified by the value for "Search Area" (in pixels), the peak of the line profile (secondary electron signal amount or secondary electron signal waveform) is searched. If the value for "Search Area" is 80, a peak is searched only within the area specified by the measuring box cursor (80 pixels) to detect an edge position. The distance between the box cursors can be increased using the "Design Value" (µm or nm) parameter to limit the edge used for measurement (or line profile peak).

Parameters "Search Area" and "Design Value" are needed to specify in which area an edge position should be searched. A mistake in determining an edge position can be prevented by specifying and limiting the area for edge detection.

In full auto measurement which uses a recipe, a measuring point is searched based on the recognition of a previously entered reference image and the box cursors are automatically positioned to perform auto measurement.

Next, values for "MP" and "Sum Lines/Point" 706 are entered. MP represents the number of line profiles to be created in the Inspect Area 703. For instance, if the value for MP is 5, five line profiles are created in a way that the Inspect Area 703 is divided into five equal parts. Sum Lines/Point 706 represents an area for secondary electron signal integration of each line profile. In this case, 60 is entered for Sum Lines/Point 706. When the abovementioned values are set in the AMP window, the conditions for creation of line profiles from an image and the area where an edge is detected can be specified.

Here, an area for integration to make one line profile is expressed in pixels. When the value for Sum Lines/Point is 60, signals equivalent to 60 pixels in the Y direction are integrated to create line profiles. As the value for Sum Lines/Point (the number of pixels) becomes larger, the amount of signals increases and signals are averaged, resulting in noise reduction.

"Inspect Area" represents an area in the Y direction where measurement is to be made; it is used to specify which area in the image is used for measurement.

The "Smoothing" parameter in the window area A (101) is used to specify the degree of smoothing for a line profile created from the image. If the value for Smoothing is 5, noise will be smaller than when no smoothing is done on the line profile. A smoothed line profile is used for edge detection in auto measurement. When linear approximation is also used for edge detection, a line profile created from the differential (inclination) of a smoothed line profile is used, so the "Differential" parameter in the window area A (101) is used to specify the differential. When the above parameters are specified in the window area A (101), all necessary conditions to create line profiles for edge detection are established. The parameters thus specified in the window area A (101) are common conditions for all auto measurement items which are entered in the AMP window. Therefore, measurement conditions for all measurement items can be easily revised just by altering relevant parameters in the window area A (101).

Figure 5:
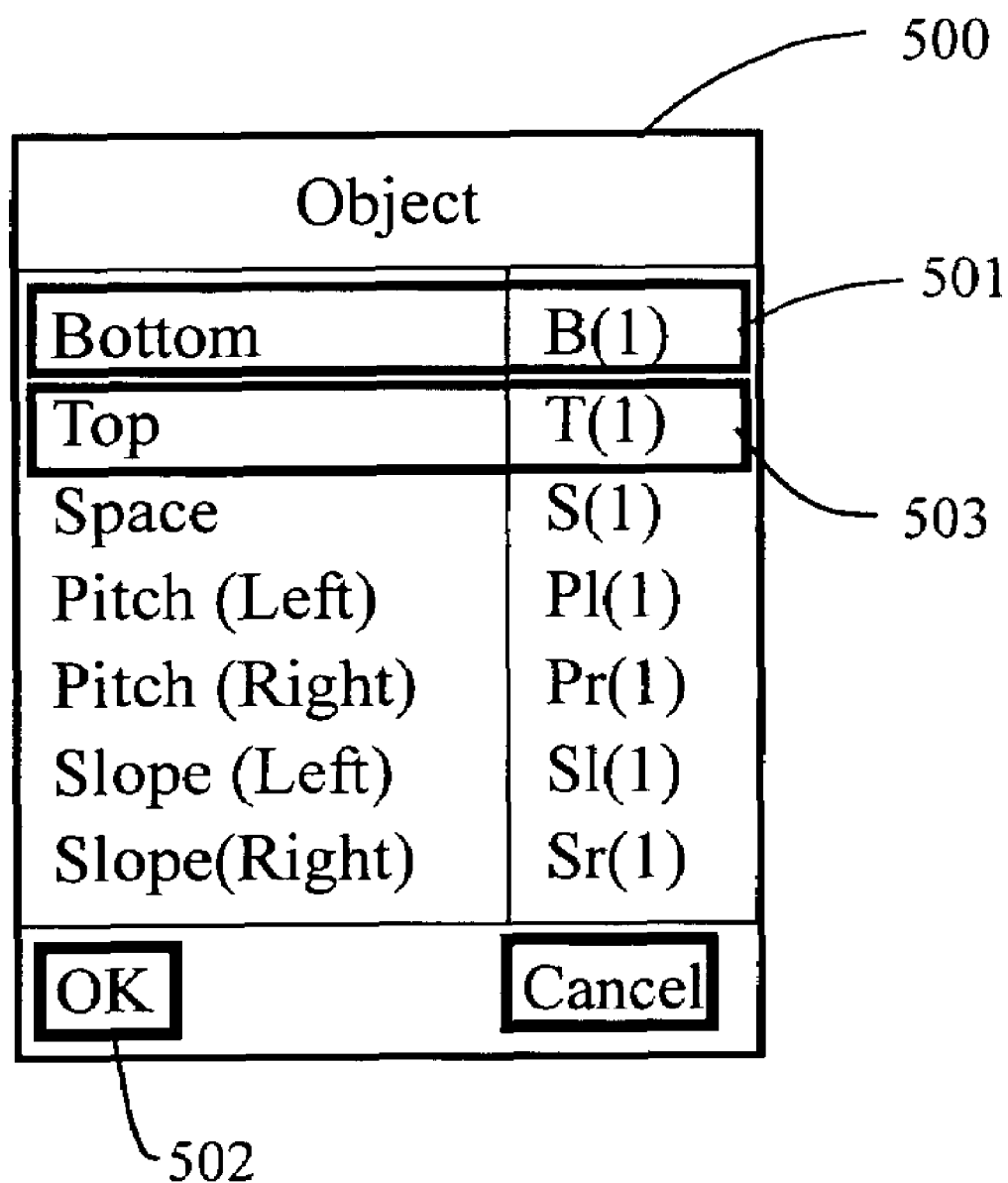
FIG. 5 shows a selection window for entry of an edge detection method.

Next, in the window area B (102) of the AMP window 100, for example, a bottom edge detection method is specified. A window 200 shown in FIG. 2 and a window 500 shown in FIG. 5 are also used here.

The window 200 in FIG. 2 appears when Bottom (B1) is chosen for Edge Detect Method and Threshold is chosen for Method. In this window, for example, the following parameters appear under "Edge Detect Parameter":

|  | Left | Right |
|---|---|---|
| Threshold | 50% | 50% |
| Edge Number | 1 | 1 |
| Base Line Start Point | — | — |
| Base Line Area | — | — |
| Edge Search Direction | Normal | Normal | and the following measurement item options appear under "Measurement Select":

| Width | Mean | W1 |
|---|---|---|
| Width | Mean' | W2 |
| Width | Max | W3 |
| Width | Min | W4 |
| Width Roughness | 3σ | WR1 |
| Width Roughness | 3σ' | WR2 |
| Width Roughness | Max-Min | WR3 |
| Edge Roughness Left | 3σ | El1 |
| Edge Roughness Left | 3σ' | El2 |
| Edge Roughness Left | Max-Min | El3 |
| Edge Roughness Right | 3σ | Er1 |
| Edge Roughness Right | 3σ' | Er2 |
| Edge Roughness Right | Max-Min | Er3 |

From these measurement items, two or more items are selected and entered in the AMP window 100 (AMP entry) in FIG. 1.

The procedure for entry of the edge detection method is as follows. First the Add button in the window area B (102) is pressed and a window 500 showing a list of edge detection object options appears as shown in FIG. 5. For example, "Bottom B (1)" 501 is selected from the list in order to make a bottom measurement and the OK button 502 is pressed. Upon press of the OK button 502, the window 200 in FIG. 2 appears in which edge detection parameters can be specified and measurement calculation and representation methods can be selected.

In the window area D (201) of the window 200, an edge detection method is selected. To use threshold data, "Threshold" is selected. When the threshold method is selected for edge detection, for example, 50% is entered as the value for Threshold. When "Normal" is selected for "Edge Search Direction" and plural edges are detected in the area specified by the parameter "Search Area," if 1 is entered for Edge Number, the edge first detected is selected. The edge detection method is thus established with the above procedure.

Next, the method of calculating a measurement from data on the edge detected by the above method is specified by selection among options under Measurement Select in a window area E (202) of the window 200. For example, in the window area E (202), W1 (Width, mean) 203 and WR1 (Width Roughness, 3σ) 204 are selected from a list of calculation/representation methods.

After the edge detection method and the measurement calculation/representation method are selected with the above procedure, the OK button 205 in the window 200 is pressed to close the window 200. Upon press of the OK button 205, B (1) appears under Edge Detect Method in the window area B (102) of the AMP window and for measurement items, W1 and WR1, each combined with B (1), appear in the window area C (103), where B (1) expresses the selected edge detection method and W1 and WR1 respectively express (mean) bottom width and width roughness (3σ) for measurement calculation.

In this way, a parameter configuration for measurement of (mean) bottom width and width roughness (3σ) is made. In order to make a parameter configuration for measurement of (mean) top width and width roughness (3σ), the Add button in the window area B (102) of the AMP window is pressed to display a list of available edge detection object options 500 and Top (T (1)) 503 is selected. Then, a procedure similar to that for bottom is carried out to make a parameter configuration for measurement of (mean) top width and width roughness (3σ).

After all the abovementioned procedures are carried out, all the entered measurement conditions appear in the AMP window 100 as shown in FIG. 1. After completion of entry of all required measurement items, the OK button 104 or the Apply button 105 of the AMP window 100 is pressed to apply the entered parameters and finish the AMP entry process.

The parameter configuration data in the AMP window 100 can be saved under a file name using a Save button 106 and the saved AMP data file can be loaded using a Load button 107. Also, an AMP data file for measurement of plural items including plural measurement calculation methods for one edge detection method can be easily generated by loading the saved AMP data file and revising the AMP configuration data and reentering it.

Given below is a procedure of confirming AMP configuration data and revising it. The parameters for creation of line profiles which are used for measurement can be easily confirmed or revised in the window area A (101) of the AMP window 100. The selected edge detection methods can also be checked in the window area B (102). Similarly, the selected edge detection method for measurement used can be confirmed from the specified measurement items in the window area C (103). When in the window area B (102) of the AMP window 100, the specified edge detection parameters are confirmed, an edge detection method which the operator wishes to revise is selected and the Edit button is pressed, or when in the window area C (103) of the AMP window a measurement item which uses the edge detection method to be revised is selected and the Edit button is pressed, an edge detection parameter configuration window appears for confirmation and revision. With this procedure for AMP entry, it is very easy to confirm and revise parameters for plural measurements.

The above embodiment concerns a case of multi point measurement of a line and space pattern. However, even when the object to be measured is, for example, a hole pattern, line profiles can be creased in a similar way though some parameters may differ; if line profile creation and edge detection are to be done, a similar AMP entry process can be used.

Figure 8:
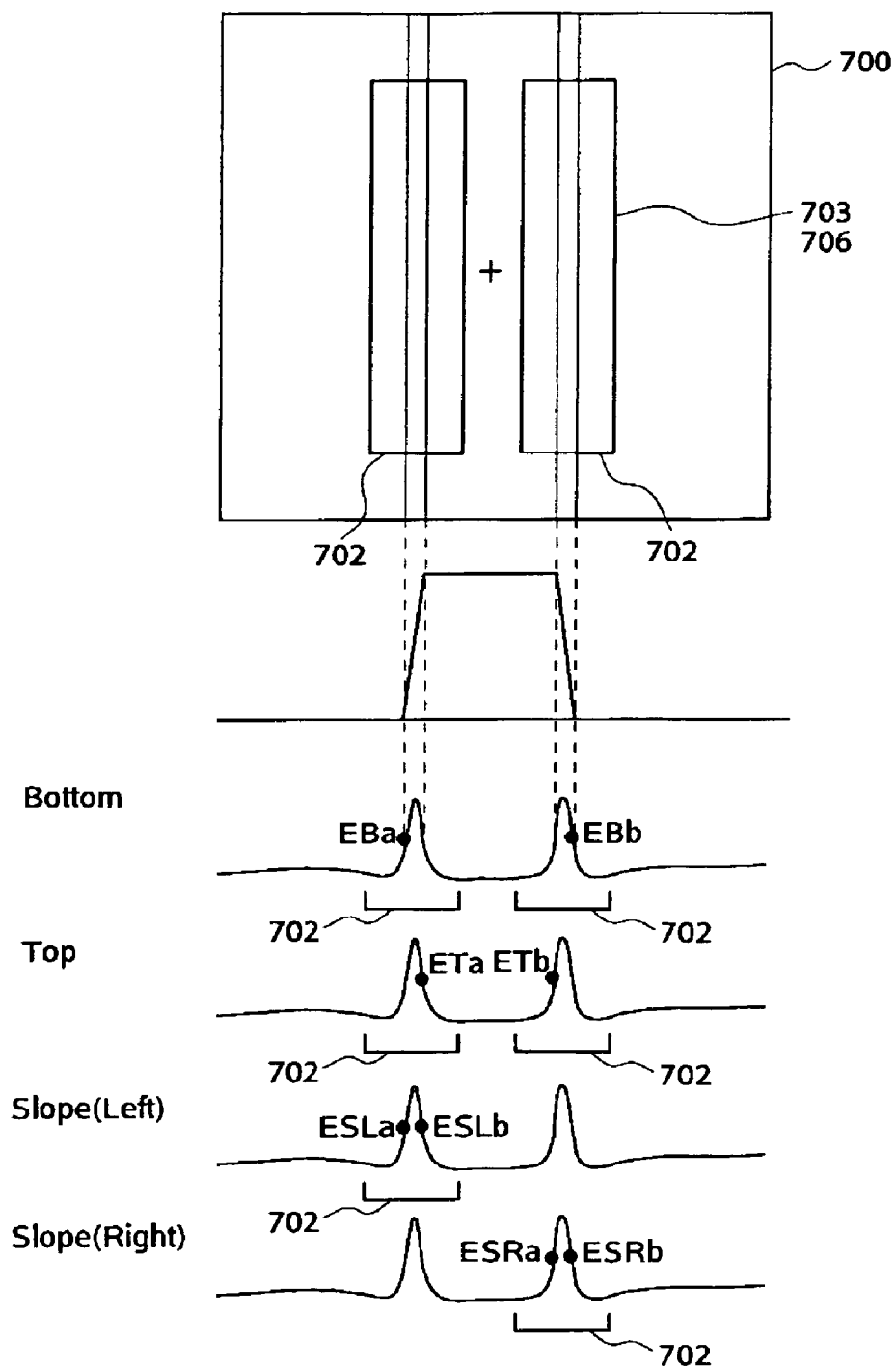
FIG. 8 illustrates detected positions and their symbols on detected signals.

Plural measurement values and roughness are shown as follows. FIG. 8 shows edge positions and their symbols for measurement of Bottom, Top, Slope (Left), and Slope (Right) of a line profile.

Figure 9:
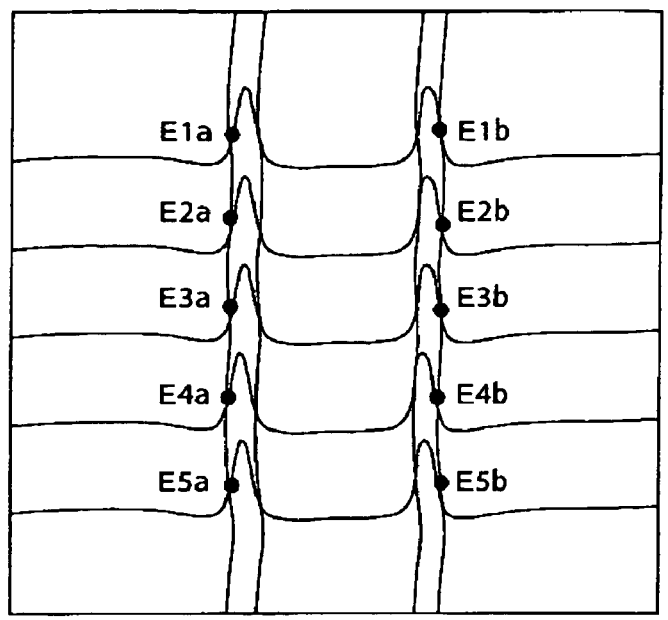
FIG. 9 illustrates a measurement calculation method on a line profile.
Figure 10:
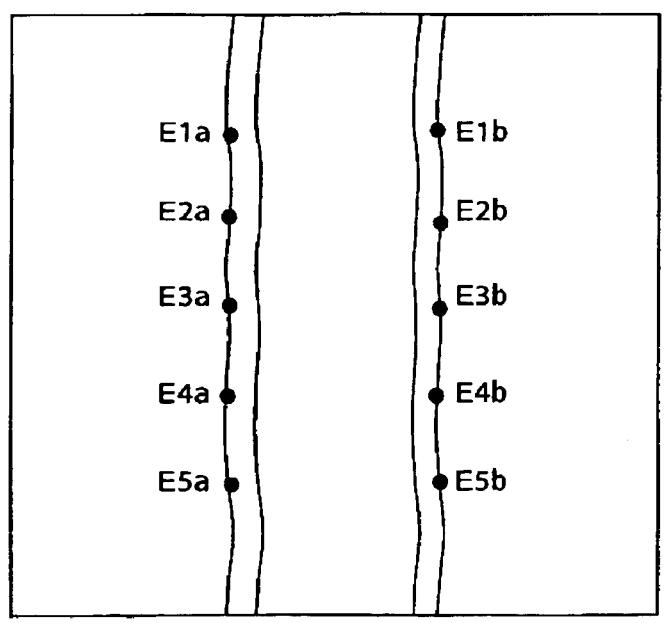
FIG. 10 shows an SEM image with detected edge positions.

As illustrated in FIG. 9 and FIG. 10, edge positions are shown with a pointing device on an SEM image and measurement is made on a measurement result representation sheet (window) or SEM image.

In this case, an edge detection method (edge symbol) and an edge position (pointing device) are shown on the SEM image simultaneously, so the edge position can be confirmed on the SEM image.

As illustrated, on a measurement result representation sheet, measurement items are each represented by a combination of a symbol for an edge detection method and a symbol for a measurement calculation/representation method. If measurement items are not known from symbols, detailed information on measurement items can be displayed by clicking or a similar method.

On the measurement result representation sheet, data is shown in a way that the order of representation of edge positions is clear. Actual measurements are shown in a way that measured parts and unmeasured parts can be distinguished.

Although a measurement result representation sheet, which typically consists of an image showing measurement results, is easy to check, it may consist of two or more images showing all measurement results.

Figure 12:
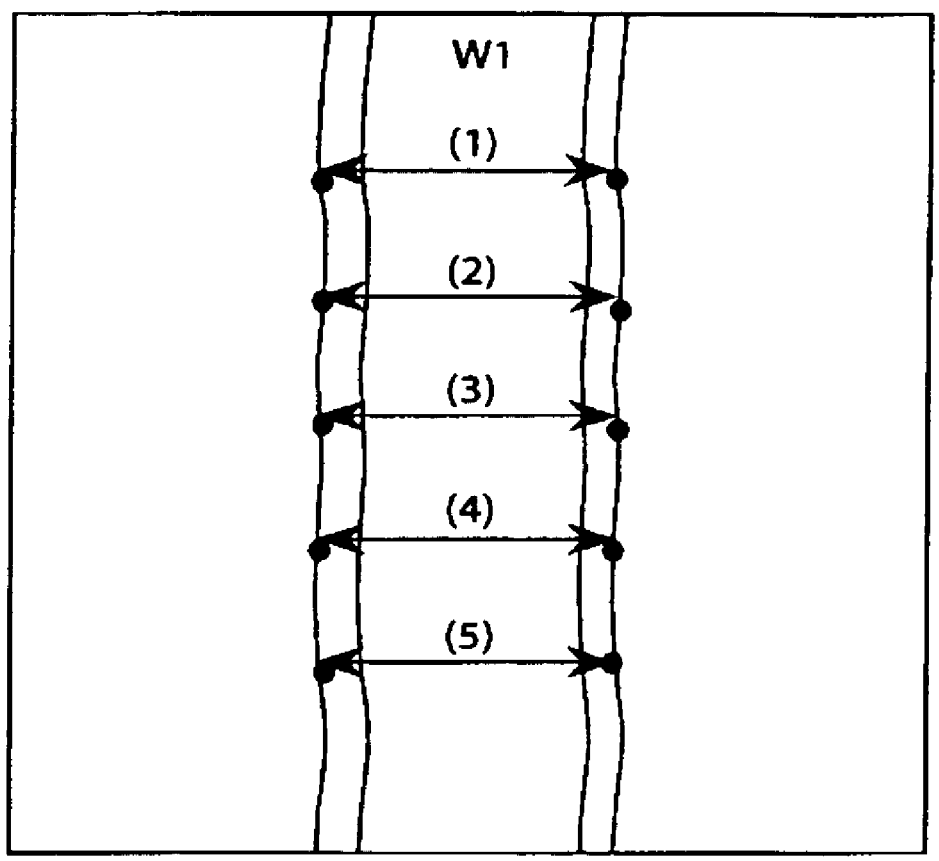
FIG. 12 illustrates one example of a mean width calculation method.

FIG. 12 illustrates a method of calculating the mean value of W1 width as an example.

This sheet displays an image showing measurement results in real time.

Detected edges and calculated (measured) parts are indicated in different fonts: for example, bold letters or a different color.

When an edge position appears in an image in real time, the edge detection method used to detect it is also indicated. For example, a rectangular frame or enclosure is used.

An image and a data sheet can be saved together as a set of data.

The saved data can be read to confirm measurement conditions, etc. in the Information window.

As mentioned so far, there is provided a scanning electron microscope with a measurement function in which plural measurement items including plural measurement calculation methods for an edge detected by an edge detection are specified in an auto measurement parameter configuration window; a line profile is created from an SEM image and edges are detected from the line profile as specified; for each detected edge, successive measurement calculations are repeated for the specified measurement items; and measurement values calculated for measurement items including plural calculation methods for an edge detection method are displayed in a display window. Also there is provided a measurement method which uses the microscope.

Furthermore, there is provided a scanning electron microscope with a measurement function in which plural measurement items including plural measurement calculation methods for an edge detected by an edge detection are specified in an auto measurement parameter configuration window; a line profile is created from an SEM image and an edge is detected from the line profile as specified; for the specified measurement items, measurements are calculated from detected edges; after plural measurements are calculated for each edge detection method, edge detection from the line profile is done for a next edge detection method; plural measurements are calculated from an edge detected for another measurement item; and measurement values calculated on plural measurement items are displayed in a display window. Also there is provided a measurement method which uses the microscope.

In the scanning electron microscope with a measurement function and the measurement method which uses it, a measurement calculation method includes such items as width and width edge roughness of a line profile.

In the scanning electron microscope with a measurement function and the measurement method which uses it, the AMP window mainly consists of three window areas: a first window area where plural measurement items are specified; a second window area where a measurement method is specified and common auto measurement parameters for all measurements are specified; and a third window area where measurement items are displayed and revised.

Figure 13:
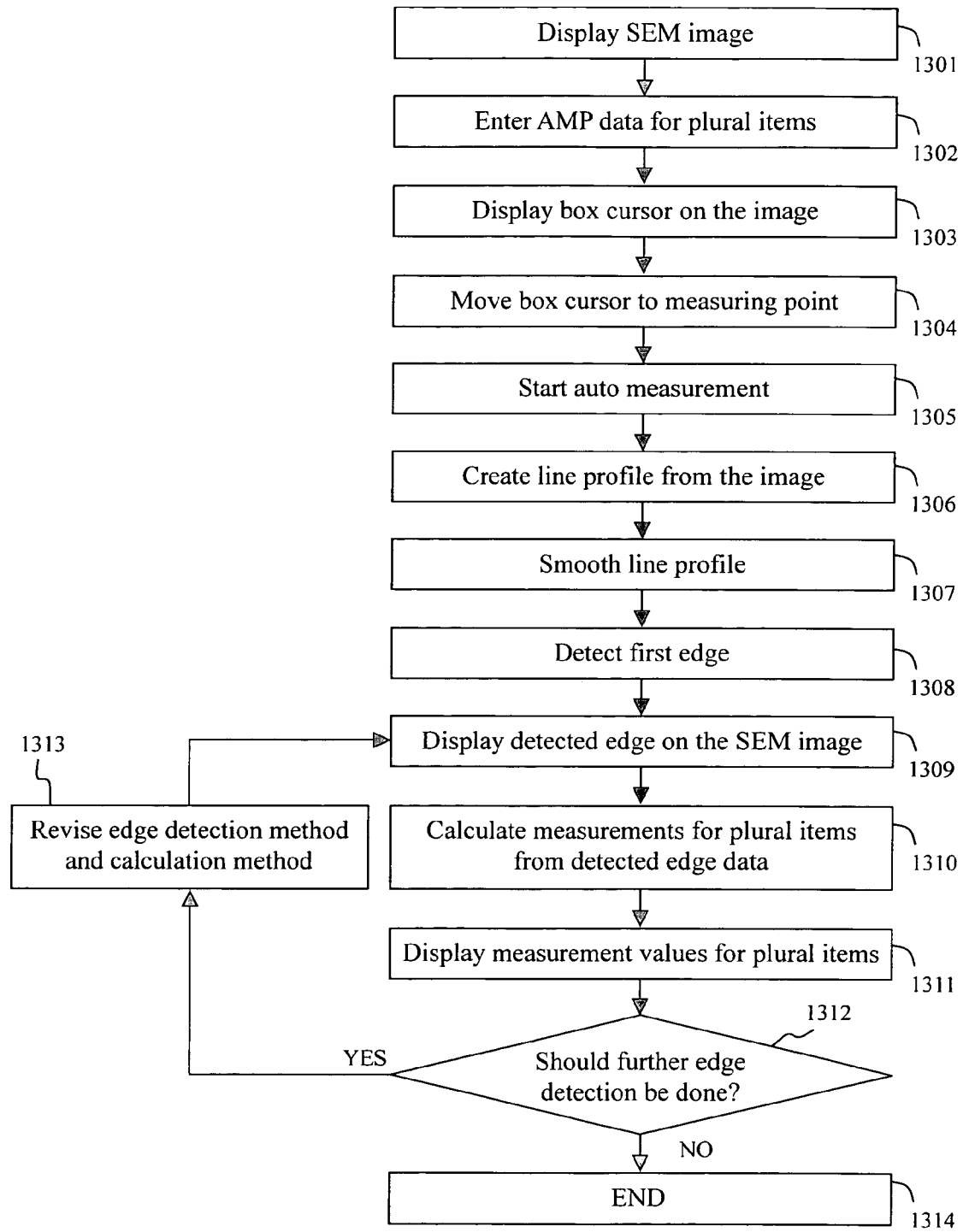
FIG. 13 is a flowchart showing a semi-auto measurement process according to the present invention.
Figure 14:
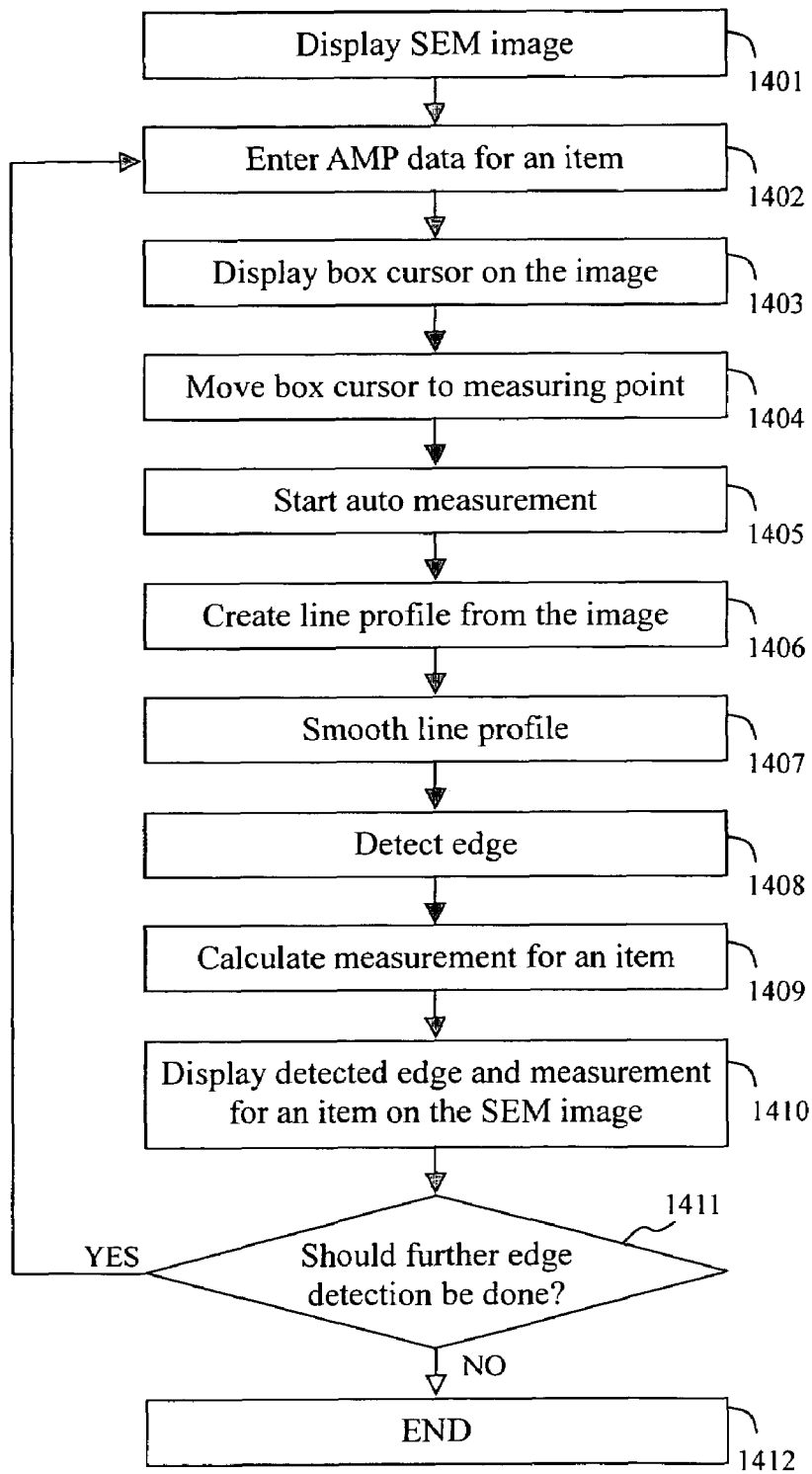
FIG. 14 is a flowchart showing a semi-auto measurement process according to the prior art.

Next, how semi-auto measurement is made using the AMP window will be explained referring to the relevant drawings. FIG. 13 is a flowchart showing a measurement sequence in a semi-auto mode according to an embodiment of the present invention. FIG. 14 is a flowchart showing a conventional measurement sequence in a semi-auto mode. First, an explanation of the measurement sequence according to the present invention is given below.

Figure 6:
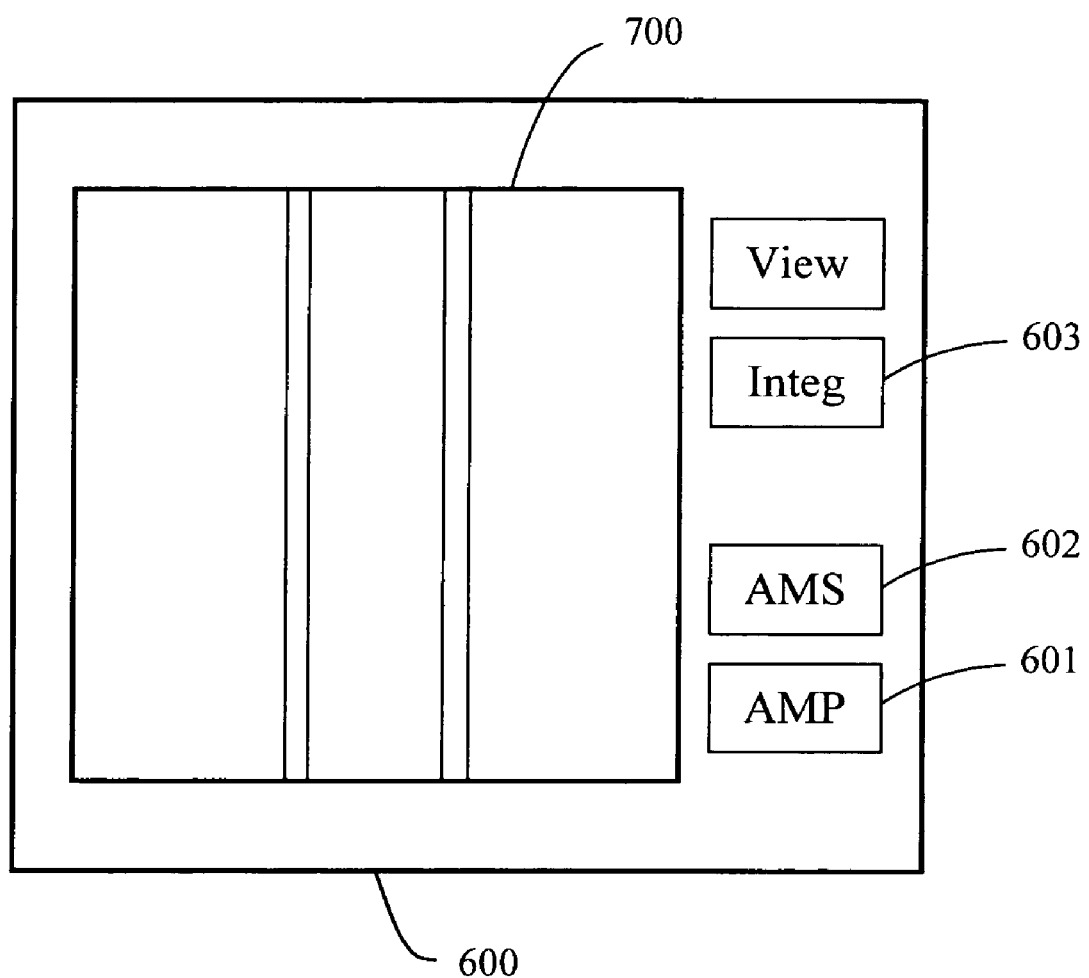
FIG. 6 shows a window for viewing an SEM image.

At step 1301, an SEM image of an object to be measured, namely a line pattern image, is displayed in the SEM image display window 600 shown in FIG. 6. An SEM image 700 is made to appear by pressing an Integ button 603 in the window 600 to irradiate the sample with an electron beam. At step 1302, measurement item data for auto measurement is entered in the AMP window and the entry is applied.

At this time, an AMP data file which has been created and saved may be loaded to make the AMP entry process easier. At step 1303, an auto measurement start button (AMS button 602) is once pressed and a box cursor appears on the SEM image. The box cursor for auto measurement is moved to a measuring point at step 1304; and the auto measurement start AMS button 602 is pressed at step 1305 to start auto measurement. In the semi-auto mode, the procedure up to this step is manually carried out. As the auto measurement start button is pressed, step 1306 and subsequent steps are all done automatically.

At step 1306, a line profile is created from the SEM image under the conditions determined by the AMP entry process. The created line profile is smoothed and differentiated at step 1307 to create a line profile for edge detection. At step 1308, using the created line profile for edge detection, edge detection is carried out by a first edge detection method specified in the AMP entry process. At step 1309, the edge detected at step 1308 is displayed on the SEM image by a point marker or the like so that it can be confirmed. According to the data on the edge detected at step 1308, measurement values are calculated by calculation methods specified in the AMP entry process at step 1310, and the calculated values are displayed in a measurement result display window or on a datasheet at step 1311.

At step 1312, if the AMP entry includes another edge detection method, edge detection method revision is made at step 1313 and using the line profile created at step 1308, another cycle of edge detection, detected edge display and measurement calculation is performed. Finally, all measurement results are saved in a storage and displayed in a measurement result display window or on a datasheet. For example, a (mean) width of the line pattern and/or width roughness will be graphically shown in the window.

Next, the conventional measurement sequence in the semi-auto mode is explained below referring to FIG. 14. At step 1401, an SEM image is displayed in an SEM image display window; at step 1402, the AMP entry process is performed. Then, a box cursor is displayed on the SEM image at step 1403 and moved to a measuring point at step 1404. As auto measurement is started at step 1405, a line profile is created from the image at step 1406 and the line profile is smoothed and differentiated at step 1407. Using the line profile thus created, edge detection is done at step 1408 and a measurement value is calculated from the detected edge at step 1409, and a marker for confirmation of the edge and a measurement result are displayed on the SEM image at step 1410. In this way, measurement for an item is made. If it is found at step 1411 that there is another measurement item, the sequence goes back to step 1402 for AMP entry and the subsequent steps must be done again.

The conventional sequence is troublesome because it is necessary to revise AMP data and start auto measurement operation for each item manually. Besides, it takes time because a line profile must be created from the image for each item. In addition, detection and display of edges are done for each item, which means that detection and display of edges have to be done many times, resulting in a long overall measurement time.

On the other hand, according to the present invention, an AMP entry process may be manually done for plural measurement items and thus once auto measurement operation is started, measurement operation for plural items is done automatically; as a consequence, it is less frequent that the operator has to revise AMP data and take the operation start procedure for auto measurement.

In terms of time required for auto measurement, a single cycle of line profile creation can be used for plural measurement items so the overall time for line profile creation can be reduced, leading to a shorter overall measurement time. Also, a single edge detection can be used for plural measurement items and therefore, in making measurement using common edge data, the number of times of edge detection and display can be decreased, leading to a shorter overall measurement time. When an image for edge confirmation is to be saved, the required number of times of save operation is equal to that of edge detection, so the number of saved images can be decreased.

An embodiment of the present invention has the following features.

1. The same number of detected edges as the number of edge detections are displayed by a pointing device on an SEM image (conventionally, an edge is indicated for each measurement item). This reduces the number of times of edge display, thereby shortening the overall measurement time.
2. A measurement item is represented by a combination of a symbol for an edge detection method (Object) and a symbol for a measurement calculation method (Measurement) (a name may be shown at the place where a symbol is indicated). Therefore, it is easy to confirm a measurement item. Whether or not common edge position data is used for measurement can be easily checked.
3. Edge detection parameters can be specified as desired and plural such parameters can be entered for an edge detection method in the AMP window. Therefore, it is possible to detect plural edges from one line profile.
4. There is a window area where parameters which are commonly used for all measurements can be specified. Therefore, all parameters can be revised at a time for plural measurement items. There is no need to revise parameters for each item.
5. Plural measurement calculation methods can be selected and entered in the AMP window. This makes the AMP entry process for plural measurement items easier.
6. Plural measurements are made by a single operation start procedure for auto measurement. Therefore, the number of AMP data revisions or the number of times of auto measurement start operation is decreased.
7. Measurement items (represented by symbols, etc) and measurement results can be displayed in a single window (on a single sheet). Therefore, it is easier to confirm measurement results.
8. In the above window, different fonts (in letter color, size, thickness, etc.) are used to distinguish between items for which measurement has been finished and items for which measurement has not been finished, so that the entered edge detection methods and the progress of measurement can be checked. Therefore, how measurement operation is progressing can be checked in real time.
9. As auto measurement operation is started, the above-mentioned measurement result display window appears. Therefore, it is easier to confirm measurement results.

According to the above embodiment, a device and a method which are described below will be realized.

A scanning electron microscope has a measurement function which uses a means to create a line profile from an image, a means to detect an edge from a line profile automatically, and a means to calculate a measurement from a detected edge to make measurements automatically according to specified auto measurement parameters (AMP), where AMP data can be entered for plural measurement items.

A scanning electron microscope may have a measurement function to enable an operator to specify auto measurement conditions for plural measurement items in a window for AMP entry.

A scanning electron microscope may have a measurement function to make measurements automatically for plural items using a common line profile.

A scanning electron microscope may have a measurement function to make measurements for plural items in an auto mode simultaneously using plural edge detection methods.

A scanning electron microscope may have a measurement function by which plural measurement values are calculated and displayed simultaneously according to plural calculation methods using data on plural detected edges.

A scanning electron microscope may have a measurement function by which the number of edge detection methods usable for plural measurement items can be increased by entering desired parameters for an edge detection method and adding it to a list of edge detection methods.

A scanning electron microscope may have a measurement function by which plural measurement values are calculated and displayed by a single operation start procedure for auto measurement.

A scanning electron microscope may have a measurement function by which measurements can be made for plural items automatically by entering plural combinations of edge detection methods and measurement calculation methods.

A scanning electron microscope may have a measurement function by which edge detection methods and measurement calculation methods are represented by symbols, letters, numerical characters and the like in a window for AMP entry.

A scanning electron microscope may have a measurement function by which a window which can display plural measurement results at a time is opened by starting auto measurement operation.

A scanning electron microscope may have a measurement function by which measurement values are displayed in a window where measurement items can be checked.

A scanning electron microscope has a measurement function which uses a means to display a line pattern image, a means to create a line profile from the image, a means to detect an edge from a line profile automatically, and a means to calculate a measurement from a detected edge to make measurements automatically according to specified auto measurement parameters. In this microscope, plural measurement items are specified in a window; for the specified plural measurement items, common parameters as auto measurement conditions are specified to create the line profile; an edge is detected from the line profile; and measurements are made automatically for plural measurement items according to data on the detected edge.

A scanning electron microscope has a measurement function which uses a means to display a line pattern image, a means to create a line profile from the image, a means to detect an edge from a line profile automatically, and a means to calculate a measurement from a detected edge to make measurements automatically according to specified auto measurement parameters. This microscope has a window which consists of three window areas: a first window area where plural measurement items are specified; a second window area where a common measurement method is specified for specified plural measurement items; and a third window area where a method of edge detection from a line profile is displayed. Here, for plural measurement items, parameters as auto measurement conditions are specified in the window.

A scanning electron microscope has a measurement function which uses a means to display a line pattern image, a means to create a line profile from the image, a means to detect an edge from a line profile automatically, and a means to calculate a measurement from a detected edge to make measurements automatically according to specified auto measurement parameters. In this microscope, plural measurement items are specified in a window; an edge is detected from the created line profile; and edge detection and measurement calculation methods are revised and auto measurements are made repeatedly and calculated measurement values are saved in a storage and, according to measurement values, a line pattern width and/or width roughness are graphically shown in the window.

What is claimed is:

1. A method for measuring the dimensions of patterns formed on a sample on the basis of a line profile which is obtained from an image formed by the electrons emitted from the patterns on the samples scanned with electron beams comprising:

for the obtained line profile, detecting edges of the patterns according to a predetermined first edge position detecting method and calculating distances between the detected edges according to a predetermined first measuring method; and for said line profile, establishing a second edge position detecting method and a second measuring method and measuring the dimensions of patterns according to the established second edge position detecting method and second measuring method.

2. The method as claimed in claim 1, wherein the measuring methods include measurement of line widths and edge roughness of the line profile.

3. A scanning electron microscope comprising a computer for measuring the dimensions of patterns formed on a sample on the basis of a line profile which is obtained from an image formed by the electrons emitted from the patterns on the samples scanned with electron beams, wherein the computer is arranged to perform a plurality of edge position detecting methods and a plurality of measuring methods for calculating distances between detected edges;

the computer detects, for the obtained line profile, edges of the patterns according to a predetermined first edge position detecting method and calculates distances between the detected edges according to a predetermined first measuring method; and the computer establishes, for said line profile, a second edge position detecting method and a second measuring method.

4. The scanning electron microscope as claimed in claim 3, wherein the measuring methods include measurement of line widths and edge roughness of the line profile.

5. The scanning electron microscope as claimed in claim 3, further comprising a display means for displaying information about the edge position detecting methods and the measuring methods.

* * * * *